United States Patent [19]

Ladyman

[11] Patent Number: 4,865,977
[45] Date of Patent: Sep. 12, 1989

[54] INCREASING MONASCUS PIGMENT PRODUCTION

[75] Inventor: Juanita A. R. Ladyman, Modesto, Calif.

[73] Assignee: Shell Oil Company, Houston, Tex.

[21] Appl. No.: 25,689

[22] Filed: Mar. 13, 1987

[51] Int. Cl.$^4$ .................... C12P 1/02; C12P 17/18
[52] U.S. Cl. .................... 435/119; 435/132; 435/170; 435/171; 435/911
[58] Field of Search ........... 435/171, 911, 170, 119, 435/132

[56] References Cited

U.S. PATENT DOCUMENTS

| | | | |
|---|---|---|---|
| 3,765,906 | 10/1973 | Yamaguchi et al. | 435/911 |
| 3,993,789 | 11/1976 | Moll et al. | 435/911 |
| 4,145,254 | 3/1979 | Shepherd et al. | 435/911 |
| 4,323,648 | 4/1982 | Tanzawa et al. | 435/911 |
| 4,418,080 | 11/1983 | Yueh et al. | 435/171 |
| 4,418,081 | 11/1983 | Rashbaum et al. | 435/171 |
| 4,442,209 | 4/1984 | Miyake et al. | 435/171 |

OTHER PUBLICATIONS

Derwent Abs. 86-141767/22, (J61078389), Riken Vitamin, (Apr. 1986).
Derwent Abs. 82-148495/08, (J57008789), Dainippon Inc., (Jan. 1982).
Derwent Abs. 81-80442D/44, (J56117794), Amano, (Sep. 1981).
Derwent Abs. 81-52636D/29, (J56065049), Hasegawa, (Jun. 1981).
Derwent Abs. 81-04658D/04, Dainippon Inc., (J55148091), (Nov. 1981).
Derwent Abs. 75-57822W/35, Ajinomoto KK, (J50046894), 4-1975.
Derwent Abs. 76-97162x/52, Ajinomoto KK, (J51130428), Nov. 1976.
Derwent Abs. 74-78245v/45, Ajinomoto, (J77027720), Jul. 1977.
Derwent Abs. 80-21206c/12, Ajinomoto KK, (J55019070), Feb. 1980.
Derwent Abs. 76-71101x/38, Toyojozo KK, (J51088519), Aug. 1976.
Carels et al., *Can. J. Microbiol.*, 24, p. 1346, (1978).
Broder et al., *J. Food Science*, 45, p. 567, (1980).
Wong et al., *J. Food Science*, 48, p. 1200, (1983).

*Primary Examiner*—Herbert J. Lilling

[57] ABSTRACT

Non-protein amino acids increase pigment production by Monascus species in the presence of protein amino acids.

26 Claims, No Drawings

INCREASING MONASCUS PIGMENT PRODUCTION

BACKGROUND OF THE INVENTION

1. Field of the Invention

The present invention is related to a method of increasing Monascus pigment production.

2. Description of the Prior Art

It is known that Monascus microorganisms produce pigments, including yellow, oranges and red-purples, that can be used to enrich or compensate for the loss of color in food processing. Chemical modifications have been attempted to decrease the problems which have prohibited the development of these pigments for practical use in the food industry. Various native materials and simple chemicals have been used and protein amino acids have commonly been found to be useful to improve the quality of the Monascus pigments.

However, it is desirable to not only improve the quality of pigment production but also to increase the amount of pigment produced.

SUMMARY OF THE INVENTION

The present invention is directed to a method of increasing pigment production by Monascus species in the presence of a free protein amino acid which method comprises treating the Monascus species in the presence of a free protein amino acid with a sufficient amount of a non-protein amino acid to increase pigment production by the Monascus species.

Any Monascus species which will produce pigment in the presence of a free protein amino acid can be used. Non-limiting representative Monascus species include M. purpureus, M. sp. 1356 and M. sp. 1361 (both obtained from the University of California, Davis, Calif.), M. major, M. rubigenosus and the like. In one embodiment of the invention the species is M. sp. 1356 or M. sp. 1361.

By free protein amino acid is meant any non-polymeric, essentially free natural amino acid commonly found in natural protein, which include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine and the natural hydroxylated derivatives thereof, including hydroxyproline and the like. The free protein amino acid can be a single free protein amino acid or functional derivative thereof which provides a useable source of free acid in the process, a mixture thereof or a composition comprising one or more of such free protein amino acids which provides a useable source of free acid to the process, including digested proteins, polypeptides and the like, such as digested gelatin, yeast, yeast extract, tomato juice and the like. For example, in one embodiment, the free protein amino acid is lysine, histidine, arginine, asparagine, threonine, glutamic acid, proline, glycine, alanine, valine, tyrosine, phenylalanine and the like. In another embodiment the source of free protein amino acid is glycine, glutamic acid, digested gelatin, yeast, yeast extract, tomato juice and the like. Preferably, the source of the free protein amino acid is yeast or yeast extract.

By free non-protein amino acid is meant a wide variety of conventionally-known non-polymeric materials containing at least one amino group and one carboxylic acid group or functional derivative thereof which provides useable source of non-polymeric, essentially free acid in the process, which materials are not commonly found as a natural amino acid component of natural protein. More than one amino or carboxylic group can be present and not necessarily in equal proportions. In one embodiment of the invention, the non-protein amino acid is an aliphatic, aryl, heterocyclic or aromatic heterocyclic compound containing at least one carboxyl group for every amino group and from 1 to 20 carbon atoms, or a functional derivative thereof, such as methanoproline, azetidine-2-carboxylic acid, p-aminobenzoic acid, aminoisobutyric acid, b-al anine and the like. Preferably, the source of free non-protein amino acid comprises one carboxylic group for each amino group and from 1 to 10 carbon atoms or a functional derivative thereof.

In another embodiment of the invention, the non-protein amino acid is a non-protein heterocyclic compound comprising one (amino-)nitrogen ring atom in an otherwise carboxylic ring containing 3 to 7 ring-carbon atoms, and at least one carboxylic acid group on the ring carbon atoms including those disclosed in U.S. Pat. Nos. 4,047,930, 4,555,260 and 4,560,401. The ring may be monocyclic or a fused bicyclic ring, and saturated or unsaturated. Preferably, the non-protein heterocyclic compound is one which comprises one (amino-)nitrogen ring-atom in an otherwise carboxylic saturated ring containing 3 to 5 ring carbon atoms and one carboxylic group on one of the ring carbon atoms. In one embodiment of the invention, the non-protein amino acid is methanoproline or, an azetidinecarboxylic acid, preferably, azetidine-3-carboxylic acid.

Functional derivative sources of either protein or non-protein amino acids include microbiologically acceptable salts, such as hydrohalide, alkali or alkaline-earth metal salts and the like or the readily decomposable ester, amide or hydrazide of such acids, including those comprising or substituted by an alkyl, alkenyl or aralkyl group of up to 10 carbon atoms.

The process of the invention is useful for the production and recovery of Monascus pigments under conditions and with growth media conventionally known and used in the art.

The amount of free protein amino acid present is that conventionally known and used in the art. Monascus sp. are usually cultured in aqueous growth media containing as little as about 0.1% wt yeast extract based on the total growth media as the source of free protein amino acid but amounts up to 1 or even 5 to 10% wt based on the total growth media in otherwise conventional kinds of growth media are within the present invention.

The amount of non-protein amino acid used to treat the Monascus species is an amount sufficient to increase pigment production by Monascus in the presence of a protein amino acid and is readily determined by simple growth test. Generally, the range of non-protein amino acid used is the same or less than the range of free protein amino acid which can be used. In one embodiment of the invention, the non-protein amino acid used in the range of about 0.001 to about 10% wt based on the total growth media. In one embodiment of the invention, the non-protein amino acid is present in the range of about 1 to 5% wt based on the total growth media.

The invention also includes a composition for producing enhanced pigment production which comprises (a) a source of Monascus species, which will produce pigment in the presence of a free protein amino acid;
(b) a free protein amino acid; and
(c) a free non-protein amino acid. The source of Monascus is conveniently a conventional culture medium containing the species. The composition conveniently comprises major amount of said culture media and the previously specified amount of each acid.

The pigments are recovered by conventional procedures known in the art to obtain the pigments usually in concentrated or freeze-dried form for convenient use as colorants, especially for food.

ILLUSTRATIVE EMBODIMENTS

The following embodiments are presented to illustrate the invention and should not be regarded as limiting it in any way.

EMBODIMENT 1

Monascus sp. 1356 was subcultured onto media slants of 5 ml containing 4% glucose. 0.3% $KH_2PO_4$, 1% yeast extract (Difco), 1.5% agar (Difco). After 7 days at room temperature, disks were cut from the slants with a cork borer. One disc was added to 50 ml of the above medium containing 1% yeast extract into which 0.02% amount of non-protein amino acids were dissolved. There were three flasks (replicates) per treatment. Prior to autoclaving, the pH of the medium was taken and was in the range 5.8–6.1. After innoculation, the flasks were placed on a shaker and left under 24 h illumination.

After 8 days incubation, the media was decanted off and, the pH was again measured. Final pH was in the range 7.1–7.6. The optical density (OD) of the media was read at 290 nm, 390 nm and 500 nm. Some samples had to be diluted to one sixth the original concentration with water. When this was necessary the OD was multiplied by the dilution factor. The mycelial mats were removed from the flasks and immediately frozen in liquid nitrogen. The mats were then wrapped in aluminum foil, freeze dried and weighed. The mats were then crumbled and a sample (50 mg) from each mat was extracted in 2 ml methanol, centrifuged and the OD determined against a methanol blank. Dilutions, up to six-fold were made when necessary.

The results of the above tests are set forth in Table I below.

TABLE I (A) Pigment Production by Monascus Treatment OD of Culture Medium into which Pigment was Secreted

|  | 290 nm | 390 nm | 500 nm |
|---|---|---|---|
| Minus Yeast Extract |  |  |  |
| Control | 0.63 | 0.26 | 0.03 |
| +Azetidine-3-carboxylic acid | 0.80 | 0.17 | 0.03 |
| +Methanoproline | 0.48 | 0.18 | 0.02 |
| +Proline | 0.84 | 0.34 | 0.04 |
| Plus Yeast Extract |  |  |  |
| Control | 2.70 | 0.76 | 0.21 |
| + Azetidine-3-carboxylic acid | 6.43 | 2.00 | 0.55 |
| +Methanoproline | 5.71 | 2.06 | 0.46 |
| +Proline | 2.93 | 0.79 | 0.17 |

(B) OD of the Extract of the Fungal Mat

|  | 290 nm | 390 nm | 500 nm |
|---|---|---|---|
| Minus Yeast Extract |  |  |  |
| Control | 2.01 | 1.94 | 0.09 |

TABLE I-continued

| +Azetidine-3-carboxylic acid | 1.93 | 0.88 | 0.16 |
|---|---|---|---|
| +Methanoproline | 1.58 | 1.66 | 0.06 |
| +Proline | 2.19 | 3.15 | 0.19 |
| Plus Yeast Extract |  |  |  |
| Control | 2.89 | 0.37 | 0.26 |
| +Azetidine-3-carboxylic acid | 7.93 | 6.30 | 2.78 |
| +Methanoproline | 7.18 | 6.30 | 2.05 |
| +Proline | 2.58 | 0.71 | 0.47 |

EMBODIMENT 2

Experimental details were similar to Embodiment 1 but incubation was of shorter duration. Concentration of the non-protein amino acids were 0.02%. Concentration of the yeast extract was 1%. The pH of the media at the beginning of the incubation ranged from 5.16 to 5.52. At the end of the incubation period the pH ranged from 4.6 to 7.0.

The results of the test are in Table 2.

TABLE 2

Pigment Production by Monascus O.D. of medium into which Pigment was Secreted

| Treatment | 290 nm | 390 nm | 500 nm |
|---|---|---|---|
| Control | 0.19 | 0.19 | 0.03 |
| +Azetidine-3-carboxylic acid | 0.70 | 0.31 | 0.07 |
| +Aminoisobutyric acid | 0.20 | 0.30 | 0.06 |
| +Beta-alanine | 1.04 | 0.37 | 0.08 |

EMBODIMENT 3

Colonies of Monascus sp. 1361 were innoculated on to solid aqueous media containing 50% tomato juice (V-8 brand name). 2% Bakers yeast, 2% agar, pH =5.7. The media also contained either 0.001%, 0.01% or 0.1% azetidine-3-carboxylic acid. The plates were then scored visually for red pigment production. Results are in Table 3.

TABLE 3

Visual Scoring of Pigment Production by Monascus

| Treatment | Score # |
|---|---|
| Control | 0 |
| +0.001% Azetidine-3-carboxylic acid | 2 |
| +0.01% Azetidine-3-carboxylic acid | 5 |
| +0.1% Azetidine-3-carboxylic acid | 9 |

0 = White: 1 = pink tinges to culture: 5 = 50% culture red
10 = 100% culture red.

Results of these experiments demonstrate that non-protein amino-acids, such as azetidine-3-carboxylic acid and methanoproline, significantly increase (red and orange) pigment production by Monascus species in the presence of free protein amino acids. The degree of stimulation is dependent upon dose of the non-protein amino acid. Related free protein amino acids, e.g. proline, do not increase pigment production to the same extent as non-protein amino acids.

What is claimed is:

1. A method of increasing pigment production by Monascus in the presence of a free protein amino acid which method comprises treating the Monascus species in the presence of free protein amino acid, which is a free protein amino acid or functional derivative thereof which provides a useable source of the free protein amino acid, a mixture of free protein amino acids or functional derivatives of free amino acids or a composition comprising one or more free protein amino acids or which provides a useable source of the free protein amino acids, with a sufficient amount of a free non-protein amino acid, which is a non-polymeric material containing at least one amino group and one carboxylic acid group or functional derivative thereof providing a useable source of the free non-protein amino acid to increase pigment production by Monascus species.

2. A method according to claim 1 wherein the Monascus species is selected from *M. purpureus, M. major* or *M. rubigenosus*.

3. A method according to claim 1 wherein the free protein amino acid is glycine, glutamic acid, digested gelatin, yeast, yeast extract, or tomato juice.

4. A method according to claim 1 wherein the protein amino acids is yeast or yeast extract or tomato juice.

5. A method according to claim 1 wherein the non-protein amino acid is an aliphatic, aryl, heterocyclic or aromatic heterocyclic compound containing at least one carboxyl group for every amino group and from 1 to 20 carbon atoms or a function derivative thereof.

6. A method according to claim 5 wherein the non-protein amino acid comprises one carboxylic group for each amino group and from 1 to 10 carbon atoms or a functional derivative thereof.

7. A method according to claim 6 wherein the non-protein amino acid is a non-protein heterocyclic compound comprising one nitrogen ring-atom in an otherwise carboxylic ring containing 3 to 7 ring-carbon atoms or a functional derivative thereof.

8. A method according to claim 7 wherein the non-protein amino acid is a non-protein heterocyclic compound comprising one nitrogen ring atom in an otherwise carboxylic saturated ring containing 3 to 5 ring carbon atoms or a functional derivative thereof.

9. A method according to claim 8 wherein the non-protein amino acid is methanoproline or an azetidine-carboxylic acid.

10. A method according to claim 8 the non-protein amino acid is azetidine-3-carboxylic acid.

11. A method according to claim 2 wherein the protein amino acid is glycine, glutamic acid, digested gelatin, yeast, yeast extract, or tomato juice and the non-protein amino acid is a heterocyclic compound comprising one-nitrogen ring atom in an otherwise carboxylic saturated ring containing 3 to 5 carbon atoms.

12. A method according to claim 11 wherein the protein amino acid is yeast or yeast extract and the non-protein amino acid is methanoproline or an azetidinecarboxylic acid.

13. A method according to claim 12 in which the non-protein amino acid is azetidine-3-carboxylic acid.

14. A composition for producing enhanced pigment production which comprises
(a) a source of Monascus species which will produce pigment in the presence of a free protein amino acid;
(b) a free protein amino acid, which is a free protein amino acid or a functional derivative thereof which provides a useable source of the free protein amino acid, a mixture of free protein amino acid or functional derivatives of the free protein amino acids or which provides a useable source of the free protein amino acids; and
(c) a free non-protein amino acid, which is a non-polymeric material containing at least one amino group and one carboxylic acid group or functional derivative thereof providing a useable source of the free non-protein amino acid, to increase pigment production by Monascus species.

15. A composition according to claim 14 wherein the Monascus species is selected from *M. purpureus, M. major* or *M. rubigenosus*.

16. A composition according to claim 14 wherein the free protein amino acid is glycine, glutamic acid, digested gelatin, yeast, yeast extract, or tomato juice.

17. A composition according to claim 14 wherein the protein amino acids is yeast or yeast extract or tomato juice.

18. A composition according to claim 14 wherein the non-protein amino acid is an aliphatic, aryl, heterocyclic or aromatic heterocyclic compound containing at least one carboxyl group for every amino group and from 1 to 20 carbon atoms or a function derivative thereof.

19. A composition according to claim 18 wherein the non-protein amino acid comprises one carboxylic group for each amino group and from 1 to 10 carbon atoms or a functional derivative thereof.

20. A composition according to claim 19 wherein the non-protein amino acid is a non-protein heterocyclic compound comprising one nitrogen ring-atom in an otherwise carboxylic ring containing 3 to 7 ring-carbon atoms or a functional derivative thereof.

21. A composition according to claim 20 wherein the non-protein amino acid is a non-protein heterocyclic compound comprising one nitrogen ring atom in an otherwise carboxylic saturated ring containing 3 to 5 ring carbon atoms a functional derivative thereof.

22. A composition according to claim 21 wherein the non-protein amino acid is methanoproline or an azetidinecarboxylic acid.

23. A composition according to claim 21 wherein the non-protein amino acid is azetidine-3-carboxylic acid.

24. A composition according to claim 15 wherein the protein amino acid is glycine, glutamic acid, digested gelatin, yeast, yeast extract, or tomato juice and the non-protein amino acid is a heterocyclic compound comprising one-nitrogen ring atom in an otherwise carboxylic saturated ring containing 3 to 5 carbon atoms.

25. A composition according to claim 24 wherein the protein amino acid is yeast or yeast extract and the non-protein amino acid is methanoproline or an azetidinecarboxylic acid.

26. A composition according to claim 25 in which the non-protein amino acid is azetidine-3-carboxylic acid.

* * * * *